United States Patent
Robinson (10) Patent No.: US 8,646,747 B1
(45) Date of Patent: Feb. 11, 2014

(54) METHODS, DEVICES, AND MEDIUMS ASSOCIATED WITH OPTICAL LIFT MECHANISM

(75) Inventor: William Neil Robinson, Sunnyvale, CA (US)

(73) Assignee: Intellectual Ventures Fund 79 LLC, Las Vegas, NV (US)

( * ) Notice: Subject to any disclaimer, the term of this patent is extended or adjusted under 35 U.S.C. 154(b) by 215 days.

(21) Appl. No.: 13/180,517

(22) Filed: Jul. 11, 2011

(51) Int. Cl.
*F16K 7/04* (2006.01)

(52) U.S. Cl.
USPC ................. 251/7; 251/11; 244/168

(58) Field of Classification Search
USPC ........................ 251/7, 11; 244/168
See application file for complete search history.

(56) References Cited

U.S. PATENT DOCUMENTS

| | | | | |
|---|---|---|---|---|
| 2,990,154 A | * | 6/1961 | Hoff ................................. | 251/7 |
| 4,637,071 A | * | 1/1987 | Pitt et al. ........................ | 398/113 |
| 5,346,372 A | * | 9/1994 | Naruse et al. .................. | 417/379 |
| 6,565,044 B1 | * | 5/2003 | Johnson et al. ............ | 244/171.5 |
| 7,913,953 B2 | * | 3/2011 | Ellinghaus ................. | 244/159.6 |
| 8,356,774 B1 | * | 1/2013 | Banik et al. ................. | 244/159.5 |
| 2003/0010869 A1 | * | 1/2003 | Kawaguchi .................... | 244/168 |
| 2003/0010870 A1 | * | 1/2003 | Chafer ........................... | 244/172 |
| 2005/0263648 A1 | * | 12/2005 | Wehner et al. ................. | 244/168 |
| 2006/0243863 A1 | * | 11/2006 | Leyre ............................ | 244/168 |
| 2011/0100478 A1 | * | 5/2011 | Allen et al. ................. | 137/15.01 |
| 2012/0228483 A1 | * | 9/2012 | Swartzlander, Jr. .......... | 250/251 |

OTHER PUBLICATIONS

Palmer, Jason; "Lightfoil Idea Shows Light Can Provide Lift"; BBC News, Science and Environment; Dec. 8, 2010; www.bbc.co.uk/news/science-environment-11927793; 3 Pages.

Swartzlander, Grover et al.; "Stable Optical Lift"; Nature Photonics, Articles; Published On; line, Dec. 5, 2010; www.nature.com/naturephotonics; 4 Pages.

* cited by examiner

*Primary Examiner* — John Rivell
*Assistant Examiner* — Matthew W Jellett
(74) *Attorney, Agent, or Firm* — Stolowitz Ford Cowger LLP (57) ABSTRACT

An apparatus includes a light foil device configured to move based on radiation pressure associated with light received by the light foil device. The apparatus includes a mechanism configured to transition between operational states in response to the movement of the light foil device, or includes a valve configured to control a flow of material through a conduit based, at least in part, on the movement of the light foil device.

41 Claims, 7 Drawing Sheets

SIDE VIEW

CROSS-SECTION

Figure 6C

SIDE VIEW

CROSS-SECTION

Figure 6D

SIDE VIEW

CROSS-SECTION

METHODS, DEVICES, AND MEDIUMS ASSOCIATED WITH OPTICAL LIFT MECHANISM

BACKGROUND

Known micro-electromechanical systems (MEMS) or other micro-circuitry may perform various functions, such as sensing pressure of a gas or liquid, detecting acceleration or gyroscopic movement, controlling ink deposit in printing operations, or the like. The known micro-electromechanical systems may be located in harsh environments, such as in a body of a human or an animal, in tires of vehicles, in containers storing hazardous and/or flammable materials, or the like, which may hinder the use of electric power supplies and degrade corresponding electronic circuitry.

DETAILED DESCRIPTION

Figure 1:
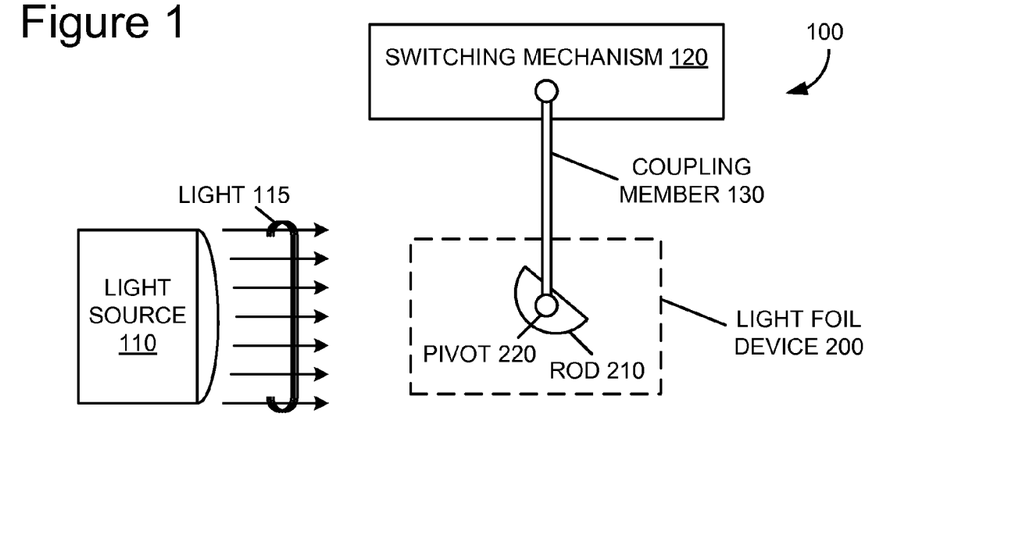
FIG. 1 depicts a block diagram of an exemplary optical lift system.

FIG. 1 depicts a block diagram of an exemplary optical lift system 100. Referring to FIG. 1, optical lift system 100 may include a light foil device 200 coupled to a switching mechanism 120, for example, via a coupling member 130. Switching mechanism 120 may transition between operational states in response to movement of light foil device 200 and coupling member 130.

Light foil device 200 may move in response to a presence of light 115 from a light source 110. Light foil device 200 may include a rod 210 configured to reflect and to refract light 115 received from light source 110. Rod 210 may comprise a light-transmissive dielectric configured to receive light 115 and one or more reflection surfaces configured to reflect and/or refract light 115 propagating through rod 210. Light 115 may exert a radiation pressure on rod 210, which may result in an optical lifting force that moves rod 210 based on the reflection and refraction of light 115. Examples of optical lift in rod 210 are discussed below in greater detail.

Coupling member 130 may be a rigid or semi-rigid structure configured to physically couple switching mechanism 120 with light foil device 200. In some examples, light foil device 200 may magnetically couple with switching mechanism 120, for example, via coupling member 130. Light foil device 200 also may include a pivot 220 coupled to rod 210 and to coupling member 130, which may allow rod 210 to rotate in response to radiation pressure from light 115, while remaining coupled to pivot 220.

Light source 110 may be activated to emit light 115 towards light foil device 200. In some examples, light 115 may be a laser beam or other focused light having a corresponding radiation pressure to move light foil device 200. Light foil device 200 may move in response to light 115, for example, in a direction corresponding to an optical lifting force. The movement of light foil device 200 may move coupling member 130, which in turn may transition switching mechanism 120 from a first operational state to a second operational state.

Light source 110 then may be deactivated to cease emitting light 115 towards light foil device 200. Light foil device 200 may move in response to the removal of light 115, for example, in a direction corresponding to a force acting on light foil device 200, such as a gravitational force, pressure from a gas, fluid, or solid material in contact with light foil device 200, or radiation pressure from a different light. The movement of light foil device 200 may move coupling member 130, which in turn may transition switching mechanism 120 from the second operational state to the first operational state, such that switching mechanism 120 is configured to transition between operational states.

Optical lift system 100 also may include an additional light source, or light source 110 may be repositioned with respect to light foil device 200, which may emit light towards light foil device 200 in a different direction than light 115. Light foil device 200 may undergo a different optical lifting force in response to light received from the different direction, and move in a direction associated with the different optical lifting force. The movement of the light foil device 200 in the direction associated with the different optical lifting force also may move coupling member 130, which in turn may cause switching mechanism 120 to transition to another operational state. For example, if no light is emitted toward light foil device 200, and then light is emitted toward light foil device 200 from the different direction, switching mechanism 120 may transition from the first operational state to a third operational state. Moreover, those of ordinary skill in the art readily will understand that any time light foil device 200 moves, switching mechanism 120 may transition from a current operational state to a new operational state.

Figure 2:
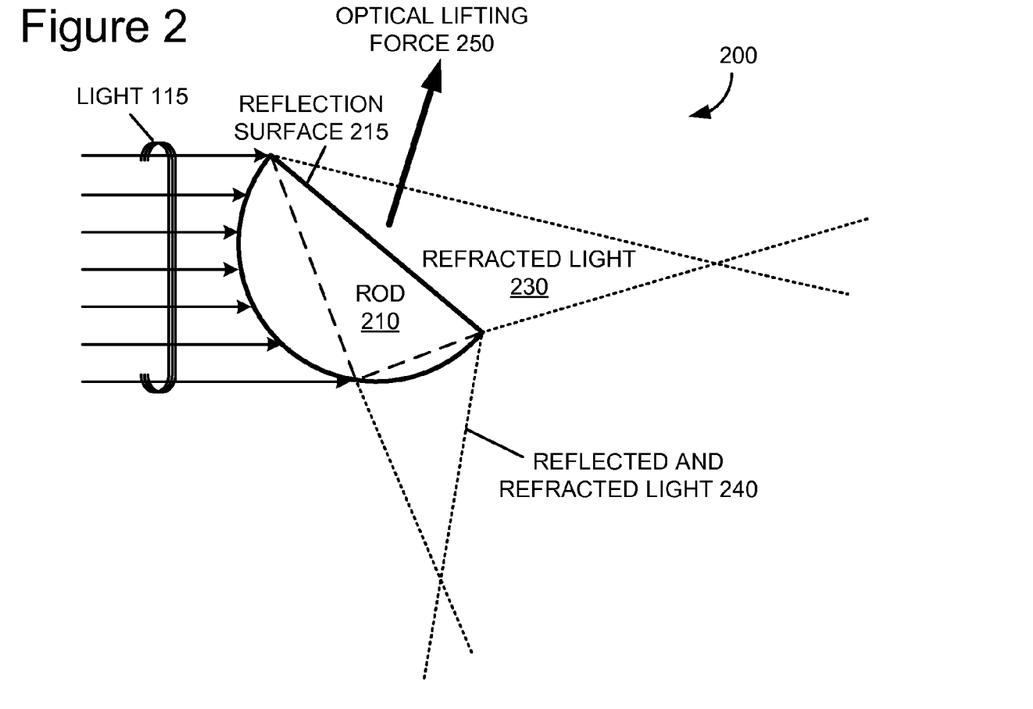
FIG. 2 depicts a block diagram of an example light foil device interacting with light.

FIG. 2 depicts a block diagram of an example light foil device 200 interacting with light 115. Referring to FIG. 2, rod 210 may have a semi-circular cross-section with a substantially planar reflection surface 215. Rod 210 may receive light 115 and refract light 115 based on dielectric properties of rod 210. Rod 210 may reflect and refract light 115 with reflection surface 215. In some examples, refracted light 230 may exit rod 210 in a direction substantially similar to a direction associated with light 115, while reflected and refracted light 240 may exit rod 210 in a direction that is substantially perpendicular to the direction of light 115 or refracted light 230. The radiation pressure exerted on rod 210 by light 115 may provide a resultant optical lifting force 250.

The radiation pressure exerted on rod 210 by light 115, in some examples, also may exert a torque on rod 210 based on directionality of light 115 with respect to rod 210. This torque may cause rod 210 to rotate, which may alter direction and magnitude of refracted light 230 and reflected and refracted light 240, as well as alter direction and magnitude of optical lifting force 250. There may be several angles or directions for light 115 to enter rod 210 that may cause rod 210 to experience little or no torque, such as when reflection surface 215 is positioned at a 45 degree angle or a 0 degree angle relative to a direction of light 115. Rod 210 may encounter a relatively stable optical lifting force 250 when there is little or no torque caused by the radiation pressure from light 115.

When light 115 has a directionality that generates torque in rod 210, the torque may cause rod 210 to rotate to a position at which light 115 generates little or no torque, such that rod 210 may utilize the torque to rotate into alignment with light 115. Rod 210 may realign a position of reflection surface 215, for example, by changing a direction of light 115 or by utilizing light from a different light source to emit light towards rod 210 from a different direction.

Although FIGS. 1 and 2 show rod 210 as having a semi-circle cross-sectional configuration, in some examples, rod 210 may have a different cross-sectional configuration, such as a rectangular cross-sectional configuration, triangular cross-sectional configuration, quadrilateral cross-sectional configuration, circular (or some fraction of a circle) cross-sectional configuration, or the like. Each of these configurations may reflect and refract light in different ways, providing various optical lifting forces to rod 210. In some examples, rod 210 also may have a substantially-straight length profile, or may be cambered or slightly curved length-wise to alter the optical lifting force and torque upon rod 210.

Figure 3A:
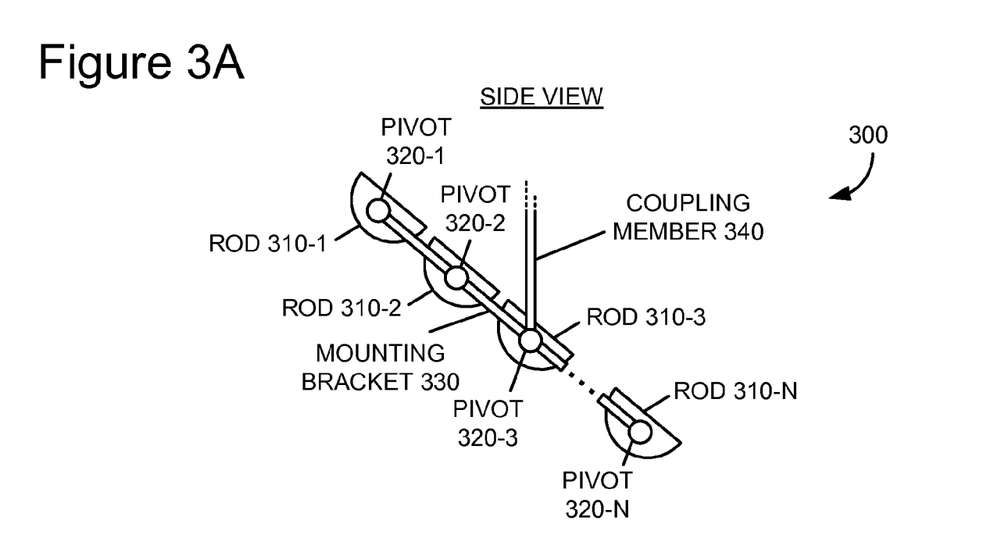
FIGS. 3A and 3B depict block diagrams of an example light foil device.
Figure 3B:
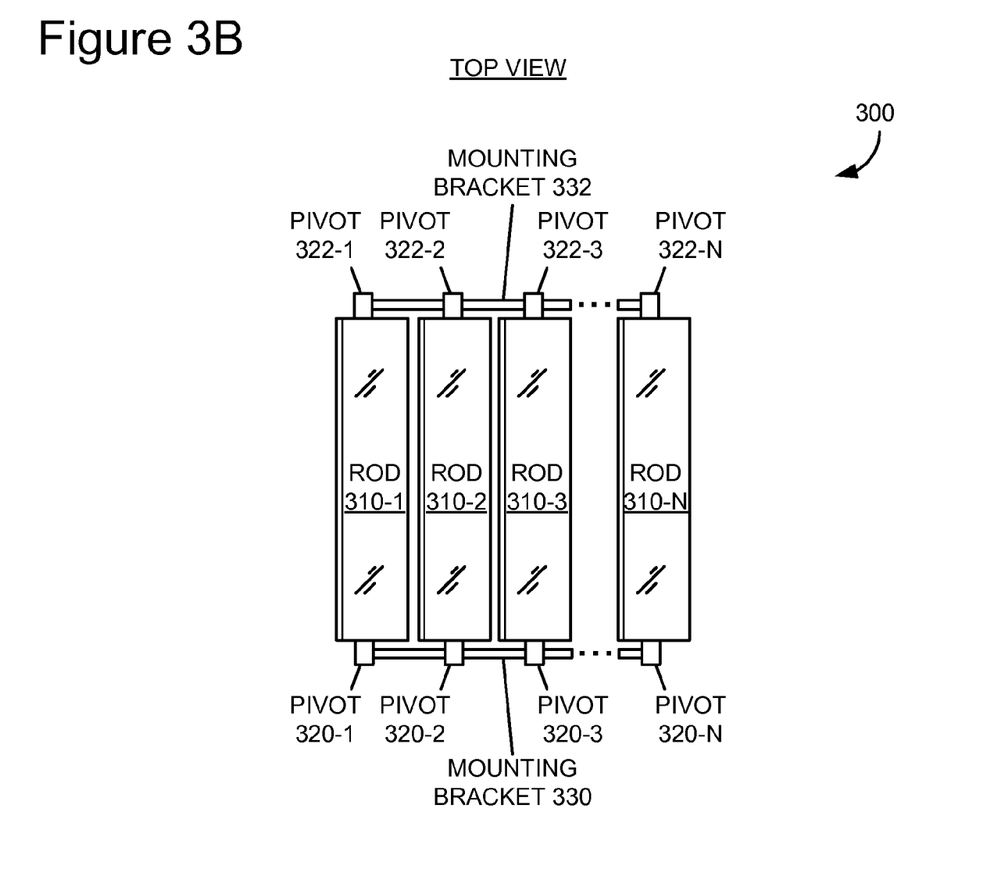

FIGS. 3A and 3B depict block diagrams of an example light foil device 300. Referring to FIGS. 3A and 3B, light foil device 300 may include rods 310-1 to 310-N arranged in a staggered configuration. The staggered configuration may allow each of rods 310-1 to 310-N to receive light emitted from a light source.

Rods 310-1 to 310-N may have a semi-circle cross-sectional configuration. In some examples, rods 310-1 to 310-N may have various cross-sectional configurations, such as a rectangular cross-sectional configuration, triangular cross-sectional configuration, quadrilateral cross-sectional configuration, circular (or some fraction of a circle) cross-sectional configuration, or the like. Each of these configurations may reflect and refract light in different ways, providing optical lifting forces to rods 310-1 to 310-N. In some examples, rods 310-1 to 310-N also may have a substantially-straight length profile, or may be cambered or slightly curved length-wise to alter the optical lifting force and torque upon rods 310-1 to 310-N.

Rods 310-1 to 310-N may be coupled to mounting brackets 330 and 332, for example, via pivots 320-1 to 320-N and 322-1 to 322-N, respectively. Pivots 320-1 to 320-N and 322-1 to 322-N may allow corresponding rods 310-1 to 310-N to rotate in response to radiation pressure from light, while remaining coupled to pivots 320-1 to 320-N and 322-1 to 322-N, respectively. Mounting brackets 330 and 332 may be coupled to a coupling member 340, for example, which may couple to switching mechanism 120 or to another device. In some examples, rods 310-1 to 310-N may be coupled to either mounting bracket 330 or mounting bracket 332, for example, via pivots 320-1 to 320-N or pivots 322-1 to 322-N, respectively.

Light foil device 300 may move in response light received by rods 310-1 to 310-N. The movement of light foil device 300 may oppose or assist a gravitational force. Rods 310-1 to 310-N may reflect and refract light, and such reflection and refraction of light may result in an optical lifting force based on a radiation pressure of the light. Rods 310-1 to 310-N may move in a direction corresponding to the optical lifting force, which also may move pivots 320-1 to 320-N and 322-1 to 322-N, mounting brackets 330 and 332, and coupling member 340. In some examples, a removal of the light received by rods 310-1 to 310-N may cause light foil device 300 to move relative to a force, for example, a gravitational force, pressure from a gas, fluid, or solid material in contact with light foil device 200, or radiation pressure from a different light. These various movements of light foil device 300 may cause switching mechanism 120 or another device to transition between operational states. Specifically, any time light foil device 300 moves, switching mechanism 120 or another device may transition from a current operational state to a new operational state.

Figure 4:
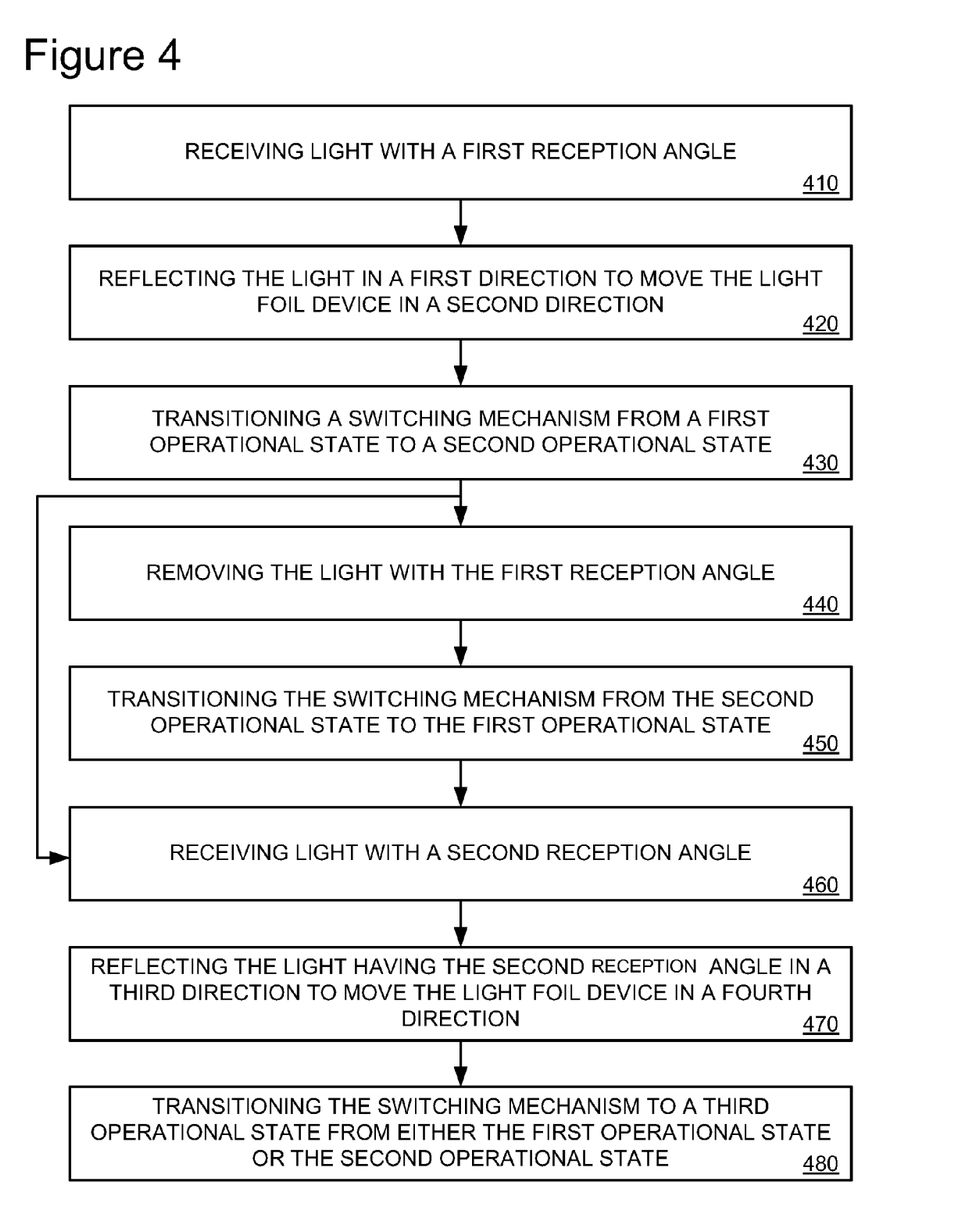
FIG. 4 depicts a flow chart of an example process for operating an optical lift system.

FIG. 4 depicts a flow chart of an example process for operating an optical lift system. Referring to FIG. 4, at operation 410, light having a first reception angle may be received. The light may be emitted from a light source, such as a laser or other focused light beam generator. In some examples, the light may be received by a light foil device, and the first reception angle may correspond to a direction the light is received by the light foil device.

At operation 420, light may be reflected in a first direction to move the light foil device in a second direction. The light foil device may include at least one rod or other light reflecting device configured to reflect the light in a direction substantially perpendicular to the direction the light was received. The reflection may cause an optical lifting force to be exerted on the light foil device substantially corresponding to the second direction based on a radiation pressure associated with the reflected light.

At operation 430, a switching mechanism may transition from a first operational state to a second operational state based on the movement of the light foil device in the second direction. The light foil device may be coupled to the switching mechanism, for example, via a coupling member. The movement of the light foil device in the second direction may cause the coupling member to move and may prompt the transition of the switching mechanism from the first operational state to the second operational state.

At operation 440, the light with the first reception angle may be removed. In some examples, the light source emitting the light may be deactivated or a direction of the light may be adjusted.

At operation 450, the switching mechanism may transition from the second operational state to the first operational state based on the movement of the light foil device in a direction corresponding to gravity. The light foil device may be coupled to the switching mechanism, for example, via a coupling member. The movement of the light foil device in the direction corresponding to gravity may cause the coupling member to move and may prompt the transition of the switching mechanism from the second operational state to the first operational state.

At operation 460, light with a second reception angle may be received. The light with a second reception angle may be from the same light source that has been repositioned, or may be from a different light source.

At operation 470, light may be reflected in a third direction to move the light foil device in a fourth direction. The light foil device may reflect the light in a direction substantially perpendicular to direction the light was received. The reflection may cause an optical lifting force to be exerted on light foil device substantially corresponding to the fourth direction based on a radiation pressure associated with the reflected light.

At operation 480, the switching mechanism may transition to a third operational state from the first operational state (transitioned to in operation 450) or from the second operational state (transitioned to in operation 430). The movement of the light foil device in the fourth direction may cause the coupling member to move and prompt the transition of the switching mechanism to the third operational state. For example, the switching mechanism may transition from the first operational state to the second operational state as a result of an activation of a light source, may transition from the second operational state to the first operational state due to gravity and as a result of the deactivation of the light source, and then may transition from the first operational state to the third operational state as a result of the reactivation of the light source with a different light emitting angle. In some examples, the switching mechanism may transition from the first operational state to the second operational state as a result of an activation of the light source, and then may transition from the second operational state to the third operational state as a result of an activation of the additional light source with the different light emitting angle.

Figure 5A:
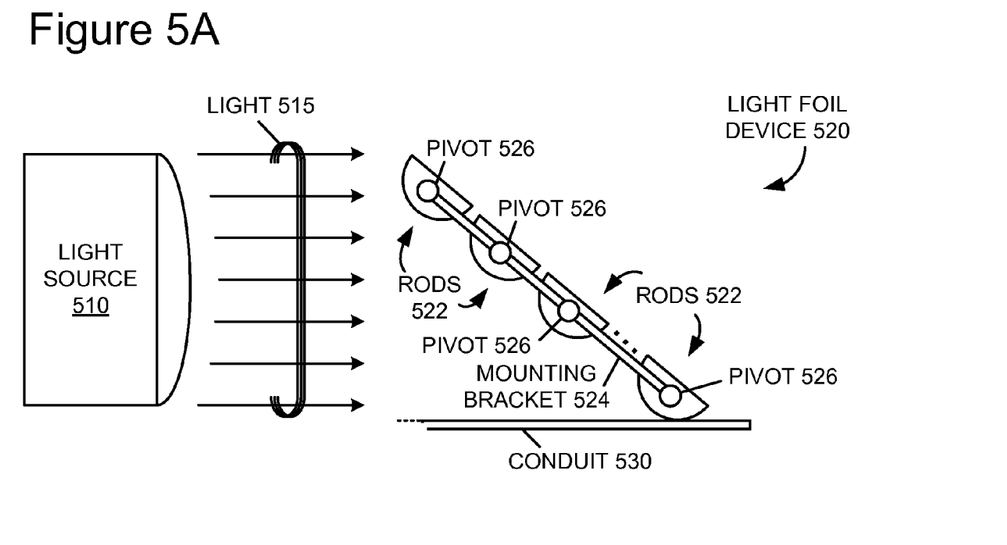
FIGS. 5A-5D depict block diagrams of an example optical lift valve system.

FIGS. 5A-5D depict block diagrams of an example optical lift valve system. Referring to FIG. 5A, a light foil device 520 may receive light 515 from a light source 510. A radiation pressure associated with light 515 may cause light foil device 520 to move.

Light foil device 520 may include rods 522 arranged in a staggered configuration. The staggered configuration may allow each of rods 522 to receive light 515 emitted from light source 510. Rods 522 may be coupled to a mounting bracket 524 via pivots 526. Pivots 526 may allow corresponding rods 522 to rotate, for example, in response to torque associated with the radiation pressure from light 515.

Optical lift valve system may include a conduit 530, such as a tube, pipe, channel, or the like, to pass material, such as liquid, gas, composition, or the like, through an opening. In some examples, conduit 530 may pass drugs in a drug dispensing device, ink in an ink jet printer, or the like. Conduit 530 may be a semi-rigid or malleable material that can flex, for example, opening or closing a passage through conduit 530, in response to contact by light foil device 520. In some examples, conduit 530 may be elastic and/or resilient and may remain open in an absence of external influence.

Figure 5B:
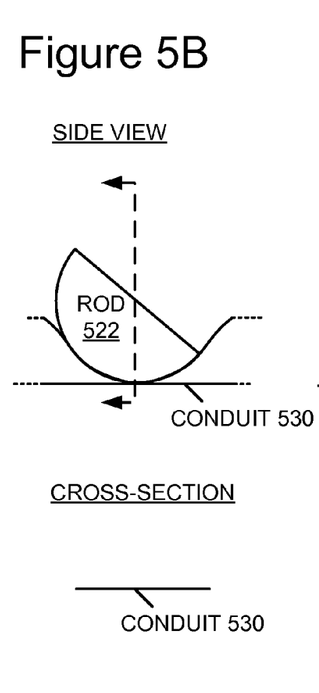
Figure 5C:
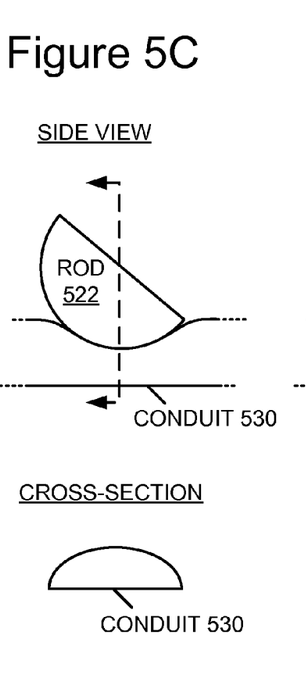
Figure 5D:
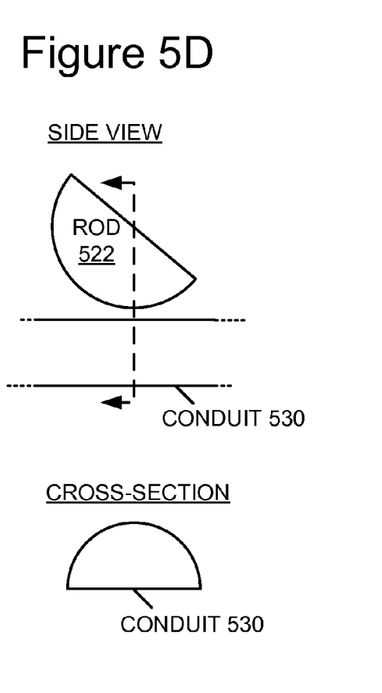

Referring to FIGS. 5B-5D, rod 522 may compress conduit 530 and close the passage for through conduit 530, as shown in FIG. 5B, for example, based on a weight of light foil device 520. In a rest state, for example, with no light 515 emitting from light source 510, light foil device 520 may close conduit 530 based on a gravitational force and the weight of light foil device 520.

Light foil device 520 may move in a direction that opposes a gravitational force in response to light 515 from light source 510. The movement of light foil device 520 may decompress conduit 530 to form an opening in conduit 530 for passage of material. The size of the opening in conduit 530 may be controlled, for example, through a control of an intensity of light 515 and/or duration of light emission by light source 510. For example, light source 510 may emit light with a first intensity, which prompts movement of light foil device 520 to create the opening in the conduit, as shown in FIG. 5C or FIG. 5D. Light foil device 520 may move based on an optical lifting force that is greater that a gravitational force.

To control the size of the opening in conduit 530, light source 510 may emit light with a second intensity, which prompts light source device 520 to stop moving. The optical lifting force corresponding to light with the second intensity may be substantially equal to the gravitational force, allowing light foil device 520 to maintain the opening in conduit 530.

Figure 6A:
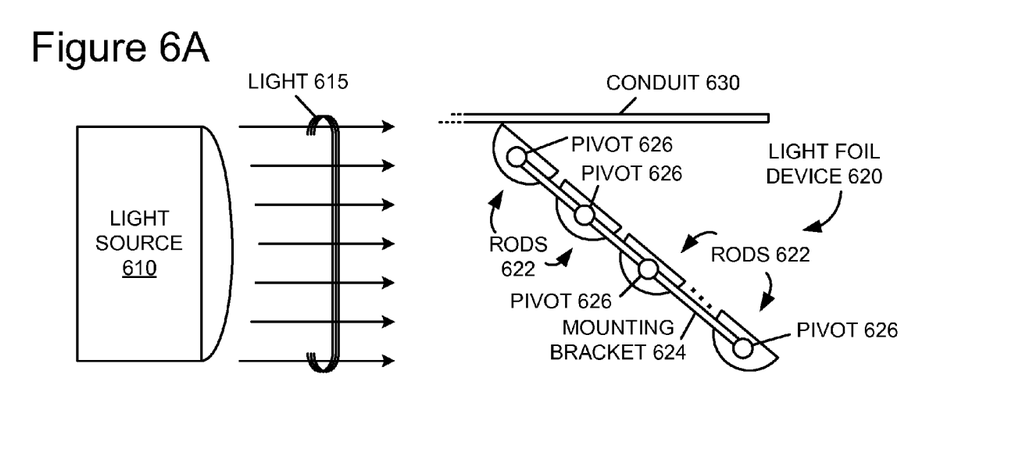
FIGS. 6A-6D depict block diagrams of operations performed by an example optical lift valve system.

FIGS. 6A-6D depict block diagrams of operations performed by an example optical lift valve. Referring to FIG. 6A, a light foil device 620 may receive light 615 from a light source 610. A radiation pressure associated with light 615 may cause light foil device 620 to move.

Light foil device 620 may include rods 622 arranged in a staggered configuration. The staggered configuration may allow each of rods 622 to receive light 615 emitted from light source 610. Rods 622 may be coupled to a mounting bracket 624 via pivots 626. Pivots 626 may allow corresponding rods 622 to rotate, for example, in response to torque associated with the radiation pressure from light 615.

Optical lift valve system may include a conduit 630, such as a tube, pipe, channel, or the like, to pass material, such as liquid, gas, composition, or the like, through an opening. In some examples, conduit 630 may pass drugs in a drug dispensing device, ink in an ink jet printer, or the like. Conduit 630 may be a semi-rigid or malleable material that can flex, for example, opening or closing a passage through conduit 630, in response to contact by light foil device 620. In some examples, conduit 630 may be elastic and/or resilient and may remain open in an absence of external influence.

Figure 6B:
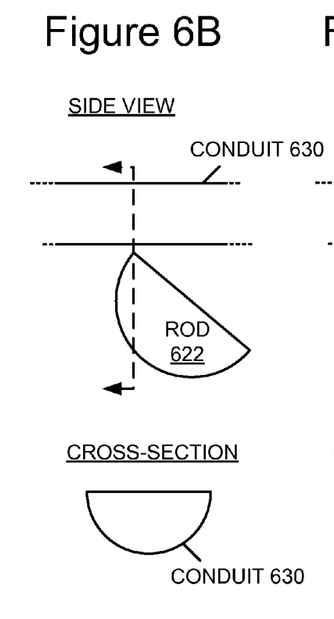
Figure 6C:
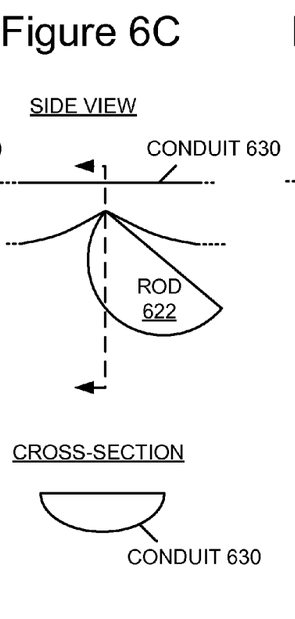
Figure 6D:
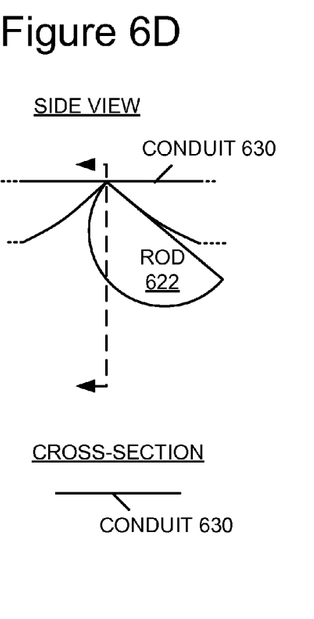

Referring to FIGS. 6B-6D, conduit 630 may be positioned above light foil device 620 and remain open in an absence of light 615. Light foil device 620 may move in a direction that opposes a gravitational force in response to light 615 from light source 610. The movement of light foil device 620 may compress conduit 630 to close a passage through conduit 630. The size of the opening in conduit 630 may be controlled, for example, through a control of an intensity of light 615 and/or duration of light emission by light source 610. For example, light source 610 may emit light with a first intensity, which prompts movement of light foil device 620 to begin closing the passage in the conduit, for example, as shown in FIG. 6C. Light foil device 620 may move based on an optical lifting force that is greater that a gravitational force. To control the size of the opening in conduit 630, light source 610 may emit light with a second intensity, which prompts light source device 620 to stop moving. The optical lifting force corresponding to light with the second intensity may be substantially equal to the gravitational force, allowing light foil device 620 maintain the opening in conduit 630. In some examples, light foil device 630 may close conduit 630, as shown in FIG. 6D, in response to light source 610 continuing to emit the light with the first intensity.

Figure 7A:
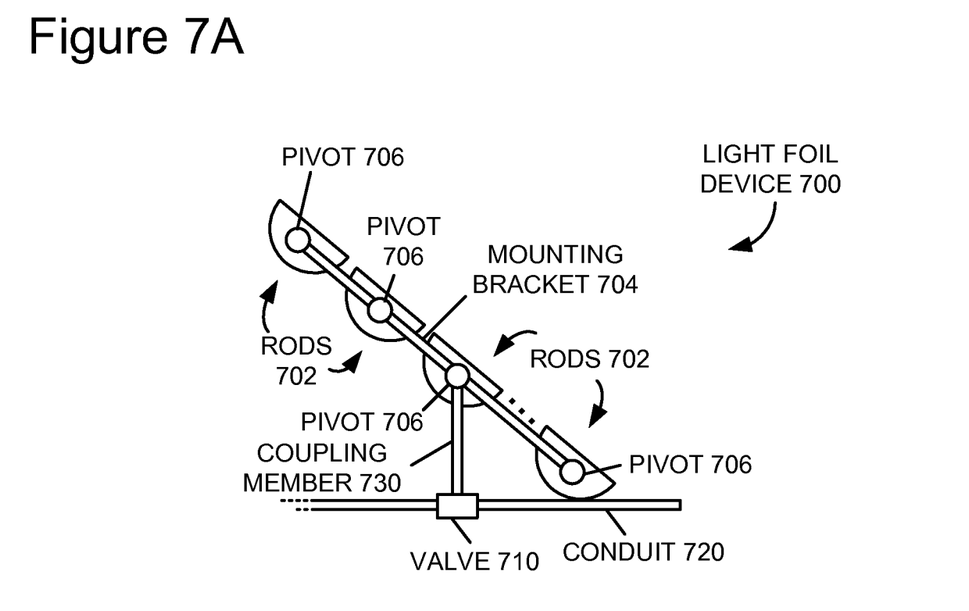
FIGS. 7A and 7B depict block diagrams of operations performed by an example optical lift valve system.
Figure 7B:
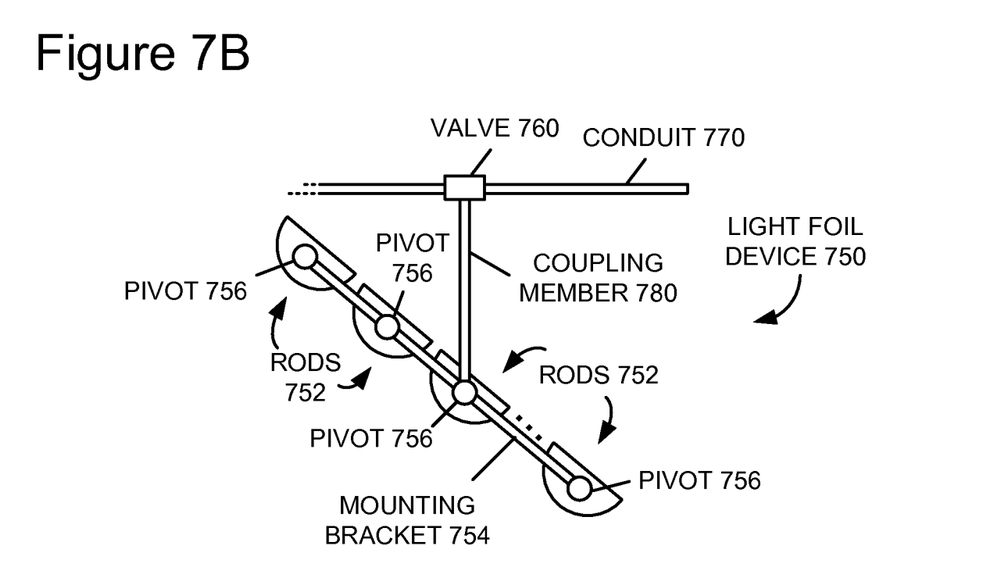

FIGS. 7A and 7B depict block diagrams of operations performed by example optical lift valve systems. Referring to FIG. 7A, an optical lift valve system may include a light foil device 700 comprising rods 702, for example, arranged in a staggered configuration. The staggered configuration may allow each of rods 702 to receive light emitted from a light source. Rods 702 may be coupled to a mounting bracket 704 via pivots 706. Pivots 706 may allow corresponding rods 702 to rotate, for example, in response to torque associated with the radiation pressure from light.

Optical lift valve system may include a conduit 720, such as a tube, pipe, channel, or the like, to pass material, such as liquid, gas, composition, or the like, through an opening. In some examples, conduit 720 may pass drugs in a drug dispensing device, ink in an ink jet printer, or the like. Conduit 720 may be a semi-rigid or malleable material that can flex, for example, opening or closing a passage through conduit 720, in response to contact by light foil device 700. In some examples, conduit 720 may be elastic and/or resilient and may remain open in an absence of external influence.

Light foil device 700 may receive light from a light source and move in response to the light. The movement of light foil device 700 may prompt a valve 710 coupled to conduit 720 to open or close, for example, via a coupling member 730. For example, a radiation pressure associated with light may cause light foil device 700 to move in a first direction, for example, away from conduit 720, which may cause valve 710 to open. Light foil device 700 may move in a second direction substantially opposite of the first direction, for example, in response to a gravitational force or radiation pressure associated with light received by light foil device 700 with a different reception angle. The movement in the second direction may cause valve to close. In some examples, valve 710 may close in response to movement of light foil device 700 in the first direction and open in response to movement of light foil device 700 in the second direction.

Valve 710 also may open or close in response to rotation of at least one rod 702 in response to light. For example, a directionality of the rotation or torque in rod 702 may indicate an operational state, for example, open or close, for valve 710 to transition. Thus, a rotation or torque associated with light foil device 700 may prompt valve 710 to transition operational states.

Referring to FIG. 7B, another optical lift valve system may include a light foil device 750 comprising rods 752 arranged in a staggered configuration. The staggered configuration may allow each of rods 752 to receive light emitted from a light source. Rods 752 may be coupled to a mounting bracket 754 via pivots 756. Pivots 756 may allow corresponding rods 752 to rotate, for example, in response to torque associated with the radiation pressure from light.

The optical lift valve system may include a conduit 770, such as a tube, pipe, channel, or the like, to pass material, such as liquid, gas, composition, or the like, through an opening. In some examples, conduit 770 may pass drugs in a drug dispensing device, ink in an ink jet printer, or the like. Conduit 770 may be a semi-rigid or malleable material that can flex, for example, opening or closing a passage through conduit 770, in response to contact by light foil device 750. In some examples, conduit 770 may be elastic and/or resilient and may remain open in an absence of external influence.

Light foil device 750 may receive light from a light source and move in response to the light. The movement of light foil device 750 may prompt a valve 760 coupled to conduit 770 to open or close, for example, through a coupling member 780. For example, a radiation pressure associated with light may cause light foil device 750 to move in a first direction, for example, towards conduit 770, which may cause valve 760 to close. Light foil device 750 may move in a second direction substantially opposite of the first direction, for example, in response to a gravitational force or radiation pressure associated with light received by light foil device 750 with a different reception angle. The movement in the second direction may cause valve to open. In some examples, valve 760 may open in response to movement of light foil device 750 in the first direction and close in response to movement of light foil device 750 in the second direction.

Valve 760 also may open or close in response to rotation of at least one rod 752 in response to light. For example, a directionality of the rotation or torque in rod 752 may indicate an operational state, for example, open or close, for valve 760 to transition. Thus, a rotation or torque associated with light foil device 750 may prompt valve 760 to transition operational states.

Figure 8:
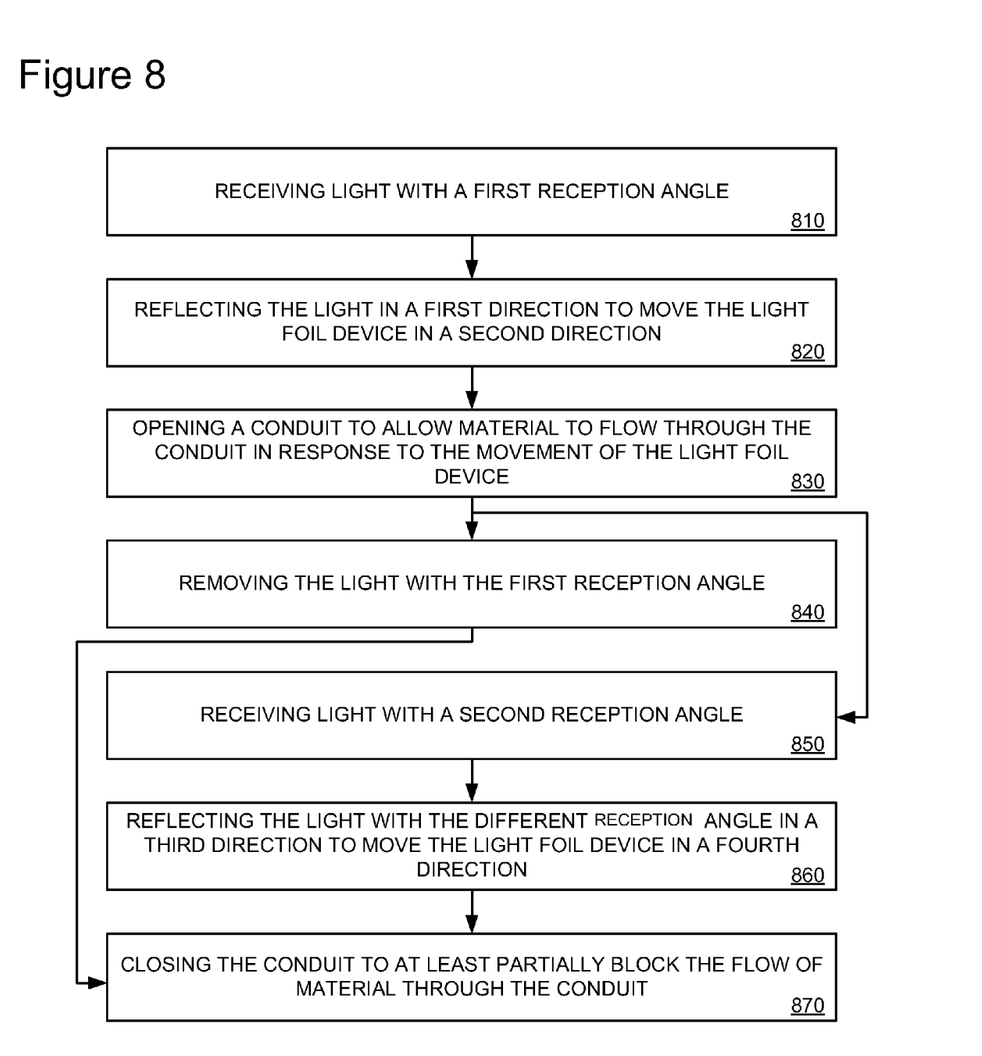
FIG. 8 depicts a flow chart of an example process for operating an optical lift valve system.

FIG. 8 depicts a flow chart of an example process for operating an optical lift valve system. Referring to FIG. 8, at operation 810, light having a first reception angle may be received. The light may be emitted from a light source, such as a laser or other focused light beam generator. In some examples, the light may be received by a light foil device, and the first reception angle may correspond to a direction the light is received by the light foil device.

At operation 820, light may be reflected in a first direction to move the light foil device in a second direction. The light foil device may include at least one rod or other light reflecting device to reflect the light in a direction substantially perpendicular to the direction the light was received. The reflection may cause an optical lifting force to be exerted on the light foil device substantially corresponding to the second direction based on a radiation pressure associated with the reflected light.

At operation 830, a conduit may open to allow material to flow through the conduit based on the movement of the light foil device in the second direction. The light foil device may be coupled to the conduit or a valve, for example, via a coupling member. The movement of the light foil device in the second direction may cause the coupling member to move and to prompt the conduit or valve to open. In some examples, the conduit may open in response to torque or a rotation of the rod caused by the reception of the light by the light foil device.

At operation 840, the light having the first reception angle may be removed. In some examples, the light source emitting the light may be deactivated or a direction of the light may be adjusted.

At operation 850, light having a second reception angle may be received. The light with a second reception angle may be from the same light source that has been repositioned, or may be from a different light source. In some examples, operation 850 may be performed after operation 830.

At operation 860, light may be reflected in a third direction to move the light foil device in a fourth direction. The light foil device may reflect the light in a direction substantially perpendicular to direction the light was received. The reflection may cause an optical lifting force to be exerted on light foil device substantially corresponding to the fourth direction based on a radiation pressure associated with the reflected light.

At operation 870, the conduit or valve may close to at least partially block the flow of material through the conduit. In some examples, the operation 870 may be performed after operation 840, for example, a gravitational force may move light foil device to cause at least partial closure of the conduit or valve. Operation 870 also may be performed after operation 860, for example, such that the movement of the light foil device in the fourth direction may cause the coupling member to move and prompt at least partial closure of the conduit or valve. The conduit also may be at least partially closed in response to torque or a rotation of the rod caused by the reception of the light by the light foil device.

The system and apparatus described above may use dedicated processor systems, micro controllers, programmable logic devices, microprocessors, or any combination thereof, to perform some or all of the operations described herein. Some of the operations described above may be implemented in software and other operations may be implemented in hardware. One or more of the operations, processes, and/or methods described herein may be performed by an apparatus, a device, and/or a system substantially similar to those as described herein and with reference to the illustrated figures.

The processing device may execute instructions or "code" stored in memory. The memory may store data as well. The processing device may include, but may not be limited to, an analog processor, a digital processor, a microprocessor, a multi-core processor, a processor array, a network processor, or the like. The processing device may be part of an integrated control system or system manager, or may be provided as a portable electronic device configured to interface with a networked system either locally or remotely via wireless transmission.

The processor memory may be integrated together with the processing device, for example RAM or FLASH memory disposed within an integrated circuit microprocessor or the like. In other examples, the memory may comprise an independent device, such as an external disk drive, a storage array, a portable FLASH key fob, or the like. The memory and processing device may be operatively coupled together, or in communication with each other, for example by an I/O port, a network connection, or the like, and the processing device may read a file stored on the memory. Associated memory may be "read only" by design (ROM) by virtue of permission settings, or not. Other examples of memory may include, but may not be limited to, WORM, EPROM, EEPROM, FLASH, or the like, which may be implemented in solid state semiconductor devices. Other memories may comprise moving parts, such as a conventional rotating disk drive. All such memories may be "machine-readable" and may be readable by a processing device.

Operating instructions or commands may be implemented or embodied in tangible forms of stored computer software (also known as "computer program" or "code"). Programs, or code, may be stored in a digital memory and may be read by the processing device. "Computer-readable storage medium" (or alternatively, "machine-readable storage medium") may include all of the foregoing types of memory, as well as new technologies of the future, as long as the memory may be capable of storing digital information in the nature of a computer program or other data, at least temporarily, and as long at the stored information may be "read" by an appropriate processing device. The term "computer-readable" may not be limited to the historical usage of "computer" to imply a complete mainframe, mini-computer, desktop or even laptop computer. Rather, "computer-readable" may comprise storage medium that may be readable by a processor, a processing device, or any computing system. Such media may be any available media that may be locally and/or remotely accessible by a computer or a processor, and may include volatile and non-volatile media, and removable and non-removable media, or any combination thereof.

A program stored in a computer-readable storage medium may comprise a computer program product. For example, a storage medium may be used as a convenient means to store or transport a computer program. For the sake of convenience, the operations may be described as various interconnected or coupled functional blocks or diagrams. However, there may be cases where these functional blocks or diagrams may be equivalently aggregated into a single logic device, program or operation with unclear boundaries.

One of skill in the art will recognize that the concepts taught herein can be tailored to a particular application in many other ways. In particular, those skilled in the art will recognize that the illustrated examples are but one of many alternative implementations that will become apparent upon reading this disclosure.

Although the specification may refer to "an", "one", "another", or "some" example(s) in several locations, this does not necessarily mean that each such reference is to the same example(s), or that the feature only applies to a single example.

The invention claimed is:

1. An apparatus comprising:
   a light foil device configured to move based on a direction of light received from a light source;
   pivots rotationally coupled to opposite ends of the light foil device;
   brackets coupled to the pivots, wherein the light foil device is configured to rotate the brackets based on the direction of the light received from the light source; and
   a mechanism coupled with the light foil device, wherein the mechanism is configured to transition between operational states in response to the rotation of the brackets.

2. The apparatus of claim 1, wherein the light foil device comprises a substantially planar surface configured to reflect the light in a first direction, and is further configured to rotate the brackets in a second direction based, at least in part, on the light reflected in the first direction.

3. The apparatus of claim 2, wherein the rotation of the brackets in the second direction transitions the mechanism into a first one of the operational states.

4. The apparatus of claim 3, wherein the light foil device is further configured to stop rotation of the brackets in response to a removal of the light.

5. The apparatus of claim 3, wherein the light foil device is further configured to rotate about the pivots and realign an orientation of the substantially planar surface to reflect the light in a third direction, and rotate the bracket in a fourth direction opposite the second direction based, at least in part, on the light reflected in the third direction, and wherein the rotation of the bracket in the fourth direction transitions the mechanism into a second one of the operational states.

6. The apparatus of claim 5, wherein the light foil device is further configured to realign the orientation of the substantially planar surface based on a reception angle associated with the light.

7. The apparatus of claim 1, further comprising a coupling member coupled at a first end to the brackets and coupled at a second end to the mechanism, wherein the coupling member is configured to actuate a valve in the mechanism in response to the rotation of the brackets.

8. The apparatus of claim 1, wherein the mechanism further comprises a switch configured to transition between an on state and an off state in response to the rotation of the brackets.

9. The apparatus of claim 1, wherein the mechanism is further configured to be magnetically coupled to the light foil device.

10. The apparatus of claim 1, wherein the light foil device further comprises a plurality of rods comprising a non-light absorbing dielectric material configured to reflect and to refract the light received by the light foil device, wherein the rods are configured to rotate the brackets based on a direction of the reflected and refracted light.

11. The apparatus of claim 10, wherein each of the rods further has a semi-cylindrical cross-section.

12. A method comprising:
    reflecting, by a light foil device, light in a first direction to move the light foil device in a second direction;
    rotating a bracket pivotally coupled to the light foil device in response to movement of the light foil device in the second direction; and
    prompting, by the light foil device, a mechanism to transition between operational states in response to the rotating of the bracket.

13. The method of claim 12, wherein prompting the mechanism to transition between operational states further comprises activating, by the light foil device, the mechanism into a first one of the operational states based on the rotating of the bracket.

14. The method of claim 13, further comprising:
    reflecting, by the light foil device, the light in a third direction to move the light foil device in a fourth direction;
    rotating, by the light foil device, the bracket in a different direction in response to movement of the light foil device in the fourth direction; and
    activating, by the light foil device, the mechanism into a second one of the operational states based on the rotating of the bracket in the different direction.

15. The method of claim 14, further comprising realigning, by the light foil device, an orientation of the light foil device to reflect the light in the third direction based on a reception angle associated with the light.

16. The method of claim 13, wherein the light foil device is configured to stop the rotating of the bracket in response to a removal of the light.

17. The method of claim 12, wherein the movement of the light foil device substantially opposes a gravitational force.

18. The method of claim 12, further comprising rotating the bracket via pivots coupled to opposite sides of the light foil device.

19. The method of claim 12, further comprising:
rotating the bracket into a first position in response to receiving a first intensity of the light;
rotating the bracket into a second position in response to receiving a second intensity of the light; and
rotating the bracket into a third position in response to receiving a third intensity of the light.

20. An apparatus comprising:
a light foil device configured to produce an optical lifting force based on a direction of light received from a light source and a direction the light is reflected and refracted by the light foil device; and
a bracket pivotally coupled to the light foil device and configured to rotate in response to the optical lifting force produced by the light foil device, wherein the rotation of the mounting bracket is configured to actuate a valve and control a flow of material through a conduit.

21. The apparatus of claim 20, wherein the optical lifting force produced by the light foil device is configured to rotate the bracket into a first position and shut off the flow of material through the conduit in response to a first angle of the light received from the light source.

22. The apparatus of claim 21, wherein the optical lifting force from the light foil device is further configured to rotate the bracket into a second position and open the flow of material through the conduit in response to a second angle of the light received from the light source.

23. The apparatus of claim 22, wherein the optical lifting force produced by the light foil device substantially opposes a gravitational force.

24. The apparatus of claim 22, wherein the optical lifting force produced by the light foil device is further configured to rotate the bracket into a third position and partially shut off the flow of material through the conduit in response to a third angle of the light received from the light source.

25. The apparatus of claim 20, further comprising pivots mounted on opposite ends of the light foil device rotationally coupling the light foil device to the bracket.

26. The apparatus of claim 20, wherein the light foil device is further configured to rotate the bracket in response to receiving the light from the light source and stop rotation of the bracket in response to removal of the light from the light source.

27. The apparatus of claim 20, wherein the light foil device is configured to:
rotate the bracket into a first position in response to receiving a first intensity of the light from the light source;
rotate the bracket into a second position in response to receiving a second intensity of the light from the light source; and
rotate the bracket into a third position in response to receiving a third intensity of the light from the light source.

28. The apparatus of claim 27, wherein the light foil device is further configured to rotate the bracket into the first position, second position, and third position based on an angle of reception corresponding to the light from the light source.

29. The apparatus of claim 27, wherein the valve is further configured to vary the flow of material through the conduit based on the first position, the second position, and the third position of the bracket.

30. The apparatus of claim 20, wherein the valve is located in at least one of an inkjet printer, a drug delivery device, or an environment immersed within an explosive material.

31. A method comprising:
moving, with a light foil device, an actuator into a first position in response to the light foil device receiving a light at a first angle;
moving, by the light foil device, the actuator into a second position in response to the light foil device receiving the light at a second angle;
moving, by the light foil device, the actuator into a third position in response to the light foil device receiving the light at a third angle; and
controlling, by a flow control system, a flow of material through a conduit based, at least in part, on the moving of the actuator into the first position, the second position, and the third position.

32. The method of claim 31, wherein controlling the flow of material through the conduit further comprises at least partially opening the conduit, by the flow control system, to allow material to flow through the conduit.

33. The method of claim 31, wherein a movement of the light foil device substantially opposes a gravitational force.

34. The method of claim 33, further comprising:
deactivating, by the flow control system, a light source from emitting the light, wherein the light foil device moves in a direction corresponding to the gravitational force in response to the deactivating; and
closing, by the flow control system, the conduit to block the flow of material through the conduit in response to the movement of the light foil device in the direction corresponding to the gravitational force.

35. The method of claim 31, further comprising:
opening, by the flow control system, the conduit to enable the flow of material through the conduit in response to the moving of the actuator into the first position;
partially closing, by the flow control system, the conduit to partially block the flow of material through the conduit in response to the moving of the actuator into the second position; and
closing, by the flow control system, the conduit to block the flow of material through the conduit in response to the moving of the actuator into the third position.

36. The method of claim 35, wherein a movement of the light foil device substantially corresponds to a gravitational force.

37. The method of claim 35, further comprising realigning a substantially planar surface of the light foil device based on receiving the light at one of the first angle, the second angle, and/or the third angle.

38. The method of claim 31, further comprising rotating, by the flow control system, the light foil device from a first orientation to a second orientation in response to changing from receiving the light at the first angle to receiving the light at the second angle.

39. The method of claim 31, further comprising suspending movement of the light foil device and holding the actuator in one of the first, second and/or third position in response to changing an intensity of the light.

40. The method of claim 31, wherein the flow control system is located in at least one of an inkjet printer, a drug delivery device, or an environment immersed within an explosive material.

41. The method of claim 31, further comprising moving, by the light foil device, the actuator into the first position, the second position, and the third position based on an intensity of the light.

* * * * *